United States Patent
Ye et al.

(10) Patent No.: US 11,039,763 B2
(45) Date of Patent: Jun. 22, 2021

(54) INTERACTIVE PHYSICAL THERAPY

(71) Applicant: Hill-Rom Services, Inc., Batesville, IN (US)

(72) Inventors: Chau Chong Ye, Singapore (SG); Yue Wang, Singapore (SG); Aye Aung, Singapore (SG)

(73) Assignee: Hill-Rom Services, Inc., Batesville, IN (US)

( * ) Notice: Subject to any disclaimer, the term of this patent is extended or adjusted under 35 U.S.C. 154(b) by 256 days.

(21) Appl. No.: 15/860,813

(22) Filed: Jan. 3, 2018

(65) Prior Publication Data
US 2018/0199861 A1  Jul. 19, 2018

Related U.S. Application Data

(60) Provisional application No. 62/445,997, filed on Jan. 13, 2017.

(51) Int. Cl.
*A61B 5/11* (2006.01)
*G16H 20/30* (2018.01)
(Continued)

(52) U.S. Cl.
CPC ........... *A61B 5/1128* (2013.01); *A61B 5/1118* (2013.01); *A61B 5/4836* (2013.01); (Continued)

(58) Field of Classification Search
CPC ... A61B 5/1128; A61B 5/1118; A61B 5/4836; G16H 20/30; A63F 13/00; G06K 9/00342
See application file for complete search history.

(56) References Cited

U.S. PATENT DOCUMENTS 7,849,043 B2 * 12/2010 Woolf .................... A63F 13/12
   706/48
8,328,691 B2 * 12/2012 Lanfermann ......... A61B 5/1114
   482/1

(Continued)

OTHER PUBLICATIONS

Home, The Straits Times, "ICU patients get better faster with early rehab," https://www.ttsh.com.sg/about-us/newsroom/news/article.aspx?id=6830, Jul. 28, 2014, 1 page.
(Continued)

*Primary Examiner* — Malina D. Blaise
(74) *Attorney, Agent, or Firm* — Merchant & Gould P.C.

(57) ABSTRACT

An example method for assisting a patient to conduct a physical therapy session can include: presenting information about the physical therapy session on a display, the information including one or more actions to be performed by the patient; capturing one or more images of the patient as the patient performs the one or more actions; detecting, by a computing device, a safety risk related to one or more medical devices associated with the patient during the physical therapy session; and providing feedback regarding the safety risk. Other methods can include: detecting, by a computing device, using the one or more images, a level of effort from the patient during the physical therapy session; and modifying a future physical therapy session for the patient based upon the level of effort; or allowing the patient to compete with other patients during the physical therapy session based upon the level of effort.

12 Claims, 6 Drawing Sheets

(51) Int. Cl.
  *G06K 9/00* (2006.01)
  *A63F 13/00* (2014.01)
  *A61B 5/00* (2006.01)

(52) U.S. Cl.
  CPC .......... *A63F 13/00* (2013.01); *G06K 9/00342* (2013.01); *G16H 20/30* (2018.01); *A61B 5/4833* (2013.01); *A61B 2505/09* (2013.01)

(56) References Cited

U.S. PATENT DOCUMENTS

| | | | |
|---|---|---|---|
| 9,098,615 B1 | 8/2015 | Tuthill et al. | |
| 9,292,935 B2* | 3/2016 | Koduri | G06K 9/00342 |
| 2002/0010595 A1* | 1/2002 | Kapp | G16H 20/10 |
| | | | 705/2 |
| 2003/0077556 A1* | 4/2003 | French | A61B 5/1113 |
| | | | 434/258 |
| 2007/0060359 A1* | 3/2007 | Smith | A63F 13/327 |
| | | | 463/42 |
| 2007/0179349 A1* | 8/2007 | Hoyme | G16H 40/63 |
| | | | 600/300 |
| 2008/0256015 A1* | 10/2008 | Woolf | A63F 13/12 |
| | | | 706/48 |
| 2009/0118100 A1* | 5/2009 | Oliver | A63B 24/0062 |
| | | | 482/8 |
| 2010/0057655 A1* | 3/2010 | Jacobson | G16H 20/30 |
| | | | 706/45 |
| 2011/0225002 A1* | 9/2011 | Fackler | G16H 40/67 |
| | | | 705/2 |
| 2011/0230263 A1* | 9/2011 | Ng | A63F 13/49 |
| | | | 463/31 |
| 2012/0109025 A1 | 5/2012 | Weinberg et al. | |
| 2012/0130740 A1* | 5/2012 | Coutinho | G16H 40/67 |
| | | | 705/3 |
| 2013/0089846 A1 | 4/2013 | Loev et al. | |
| 2013/0282395 A1* | 10/2013 | Rustgi | G16H 20/60 |
| | | | 705/2 |
| 2014/0081432 A1* | 3/2014 | Kingon | G05B 15/02 |
| | | | 700/90 |
| 2014/0100464 A1* | 4/2014 | Kaleal | A61B 5/0205 |
| | | | 600/508 |
| 2014/0122494 A1* | 5/2014 | Thurston | G06F 16/24578 |
| | | | 707/738 |
| 2014/0336943 A1* | 11/2014 | Pellini | G16H 10/60 |
| | | | 702/19 |
| 2015/0004581 A1 | 1/2015 | Selman et al. | |
| 2015/0066174 A1* | 3/2015 | Dugan | A63F 13/816 |
| | | | 700/91 |
| 2015/0066956 A1* | 3/2015 | Chae | G06F 16/244 |
| | | | 707/749 |
| 2015/0112702 A1* | 4/2015 | Joao | G16H 15/00 |
| | | | 705/2 |
| 2015/0148113 A1* | 5/2015 | Klein | G06F 19/3481 |
| | | | 463/7 |
| 2015/0196804 A1* | 7/2015 | Koduri | G06K 9/00342 |
| | | | 482/8 |
| 2015/0196805 A1* | 7/2015 | Koduri | A63B 24/0087 |
| | | | 482/6 |
| 2015/0202492 A1* | 7/2015 | Domansky | A63F 13/00 |
| | | | 434/257 |
| 2015/0296044 A1* | 10/2015 | Liu | G06Q 30/02 |
| | | | 709/204 |
| 2016/0129335 A1* | 5/2016 | Domansky | G06K 9/00348 |
| | | | 348/77 |
| 2016/0129343 A1* | 5/2016 | Domansky | A63F 13/428 |
| | | | 463/7 |
| 2016/0139661 A1* | 5/2016 | Kim | A63F 13/31 |
| | | | 463/37 |
| 2016/0256771 A1* | 9/2016 | Ekbia | A63F 13/21 |
| 2017/0225032 A1* | 8/2017 | Jones | A63B 71/148 |
| 2017/0304705 A1* | 10/2017 | Hermandorfer | A63B 71/02 |
| 2017/0360356 A1* | 12/2017 | Ashdown | G06F 7/06 |
| 2018/0001184 A1* | 1/2018 | Tran | G06F 1/163 |
| 2018/0056130 A1* | 3/2018 | Bitran | G06F 19/3418 |
| 2018/0227706 A1* | 8/2018 | Cho | G16H 40/60 |
| 2018/0288119 A1* | 10/2018 | Lee | H04L 67/22 |
| 2019/0224528 A1* | 7/2019 | Omid-Zohoor | G16H 50/20 |
| 2020/0219619 A1* | 7/2020 | Feczko | G16H 20/70 |

OTHER PUBLICATIONS

The Straits Times, "Machines give rehab patients a leg-up, reminders and more," http://www.straitstimes.com/singapore/health/machines-give-rehab-patients-a-leg-up-reminders-and-more, Jul. 24, 2015, 3 pages.

* cited by examiner

INTERACTIVE PHYSICAL THERAPY

RELATED APPLICATION(S)

This patent application claims the benefit of U.S. Patent Application Ser. No. 62/445,997 filed on Jan. 13, 2017, the entirety of which is hereby incorporated by reference.

BACKGROUND

Patients in an Intensive Care Unit (ICU) setting are usually frail in both physical status and mental status. The conventional impression of ICU patients is that they lie in bed to recuperate. However, for each day the patients lie in bed, they can lose muscle mass. Research shows that patients who start physical therapy earlier in their recoveries can leave the ICU more quickly. Surveys also show that patients are happy to get out of the bed, as lying in bed for prolonged periods can lead to fatigue. However, physical therapy can be labor-intensive, and resources for well-trained physical therapists are typically limited.

SUMMARY

Figure 1:
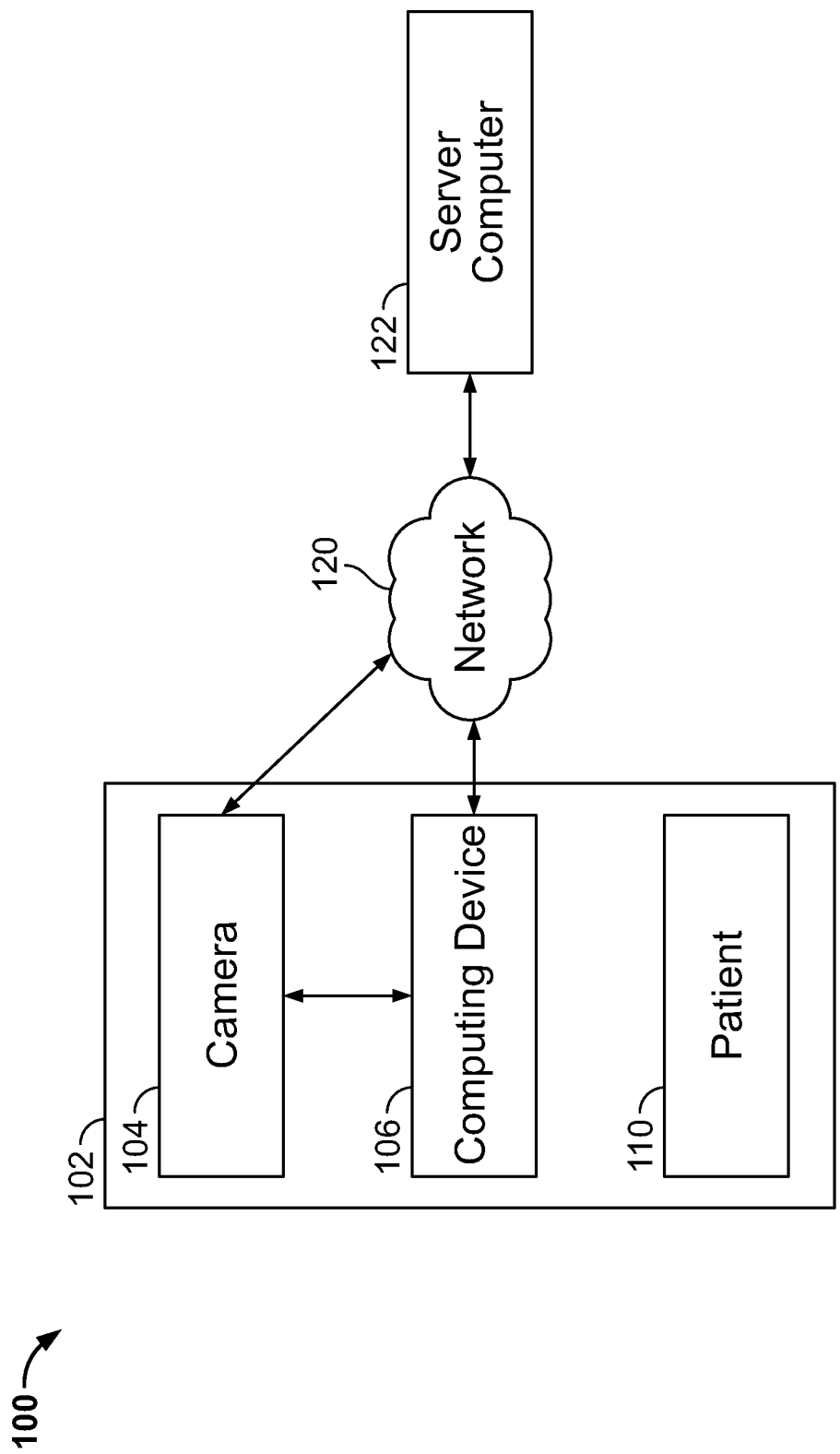
FIG. 1 shows an example system including a patient and a computing device programmed to assist the patient in conducting physical therapy.

In one aspect, an example method for assisting a patient to conduct a physical therapy session includes: presenting information about the physical therapy session on a display, the information including one or more actions to be performed by the patient; capturing one or more images of the patient as the patient performs the one or more actions during the physical therapy session; detecting, by a computing device, using the one or more images, a safety risk related to one or more medical devices associated with the patient during the physical therapy session; and providing feedback regarding the safety risk.

In another aspect, an example method for assisting a patient to conduct a physical therapy session includes: presenting information about the physical therapy session on a display, the information including one or more actions to be performed by the patient; capturing one or more images of the patient as the patient performs the one or more actions during the physical therapy session; detecting, by a computing device, using the one or more images, a level of effort from the patient during the physical therapy session; and modifying a future physical therapy session for the patient based upon the level of effort.

In yet another aspect, an example method for assisting a patient to conduct a physical therapy session includes: presenting information about the physical therapy session on a display, the information including one or more actions to be performed by the patient; capturing one or more images of the patient as the patient performs the one or more actions during the physical therapy session; detecting, by a computing device, using the one or more images, a level of effort from the patient during the physical therapy session; and allowing the patient to compete with other patients during the physical therapy session based upon the level of effort.

DETAILED DESCRIPTION

The present disclosure is directed to systems and methods for assisting a patient in conducting physical therapy.

The examples described herein may provide a less labor-intensive process for physical therapy that can be attractive and beneficial to both caregivers and patients. In these examples, a computing device including a display is used to guide and engage the patient in a physical therapy session. A motion sensing device captures the actions of the patient and those actions are analyzed. Feedback can be delivered to the patient (and/or the patient's caregiver) to achieve a desired outcome from the physical therapy. Such feedback can include information about the patient's performance, such as more accurate postures, patient compliance, and/or ultimately be used to customize future physical therapy sessions for the patient.

In one embodiment, an interactive display is controlled by a computing device and is used to demonstrate a physical therapy session to a patient. A patient can follow the steps on the display to do the physical therapy, and one or more cameras capture the patient's posture and relative location to various items in the patient's environment, such as ventilator tubes and central lines.

The information captured by the cameras can be used to provide monitoring and audio/visual feedback for the patient to, for example, make adjustment(s) to the physical therapy routine, if required. In some examples, a video processing algorithm is used to analyze the data captured by the cameras to automatically assess the patient's efforts and load during the physical therapy, and to possibly customize the physical therapy for the patient depending on the patient's condition and tolerance. In other examples, the data can also be used to analyze and assess possible hazardous conditions created by the physical therapy, such as undue stress placed upon the patient and/or identification of safety or risky concerns relative to the patient's therapy and environment.

In some examples, one or more gaming components are added to the system. This can include the addition of awards and/or social media aspects for the patient. By adding gaming components (i.e., gamification), the system can be used to engage multiple patients simultaneously to compete with each other. This type of social interaction can enhance the physical therapy by making the patients more engaged in the process.

Figure 2:
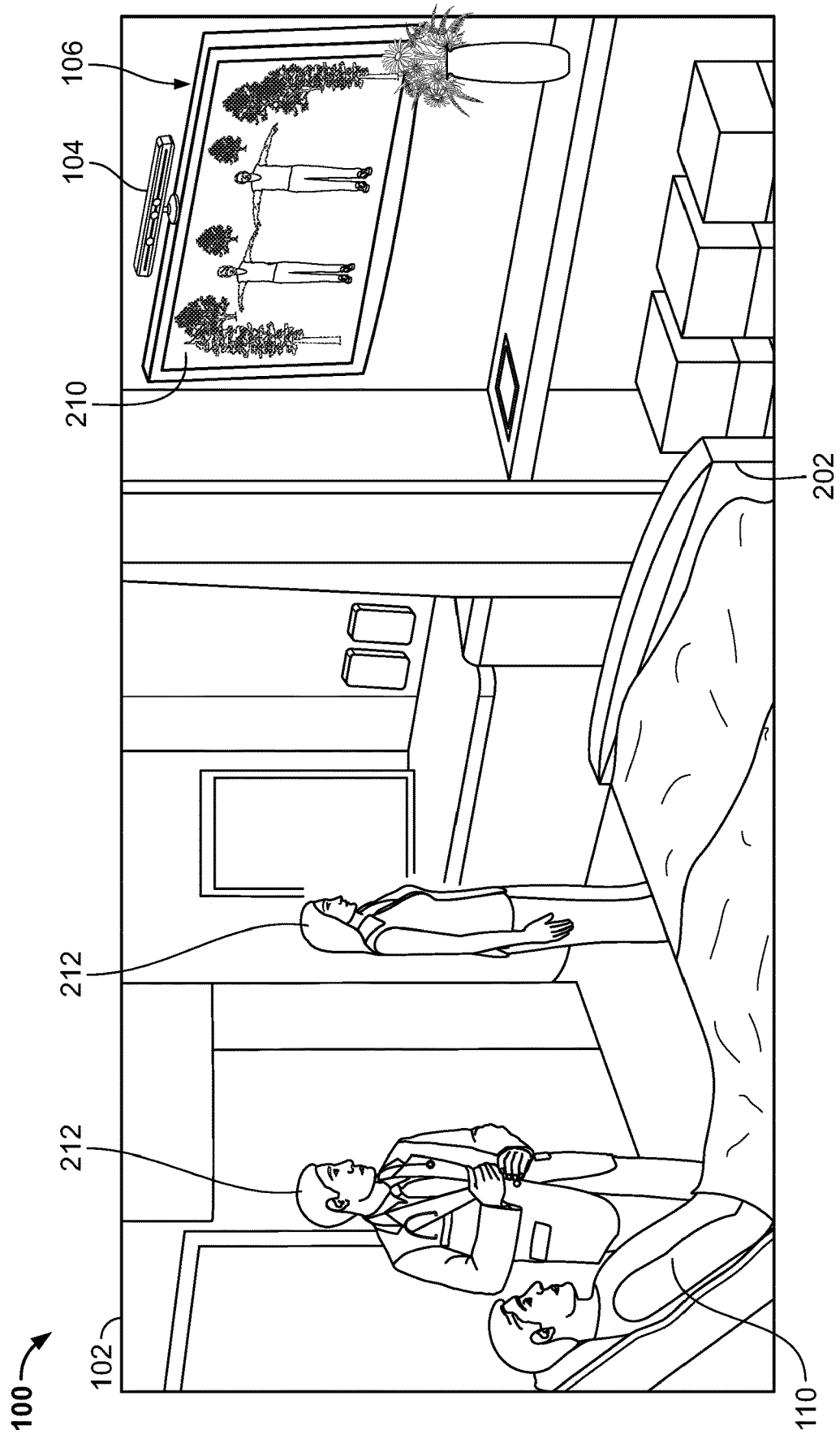
FIG. 2 shows additional details of the system of FIG. 1.

Referring now to FIGS. 1-2, an example system 100 is shown. In the system 100, a patient 110 is located in an environment 102, such as a hospital room, clinical setting, or bedroom. The environment 102 also includes one or more cameras 104 and a computing device 106.

The patient 110 is typically supported by a patient support device 202, such as a bed, that can be used in some embodiments to assist the patient 110 to carry out physical therapy actions. One example of such a patient support device 202 is the Total Care® P500 Intensive Care Bed manufactured by Hill-Rom of Batesville, Ind. In other examples, the patient 110 can be supported by other devices (e.g., wheel chair, crutches) and/or be self-supported (e.g., be standing). Other configurations are possible.

The computing device 106 can be coupled to the patient support device 202 or positioned elsewhere in the environment 102 (such as coupled to a wall, as illustrated in FIG. 2). The computing device 106 includes a display 210 to illustrate various aspects of a physical therapy session to the patient 110. A physical therapy session can be a set of interactions between the computing device 106 and the patient 110 that functions to provide physical therapy benefits to the patient 110. This can include both information and specific actions for the patient 110 to perform. Caregivers 212 and/or possibly the patient support device 202 can help facilitate the physical therapy sessions, especially during the initial stages.

For example, the display 210 of the computing device 106 displays information to the patient 110, as well as illustrative actions to accomplish the physical therapy session. The patient 110 watches the information on the display 210 and performs the actions. The patient 110 can perform such actions while positioned on the patient support device 202 or in other positions, such as standing, sitting, etc.

If positioned on the patient support device 202, the patient support device 202 can assist the patient 110 with the physical therapy. For example, the patient support device 202 can manipulate aspects of the patient's posture by, for example, causing the head of the bed to rise to position in the patient in a sitting position if the patient cannot leave the bed. In some examples, the patient support device 202 can be controlled directly by the computing device 106 to manipulate certain aspects of the patient's posture during the physical therapy session. In other examples, the bed is controlled manually.

The camera 104 is positioned within the environment 102. The camera 104 can be a standalone device or can be coupled to other structures within the environment 102, such as a wall as shown in FIG. 2. In yet other embodiments, the camera 104 can be integrated within the computing device 106.

In this example, the camera 104 is an infrared camera configured to capture infrared images and/or video of the patient 110 on the patient support device 202. The camera 104 includes an infrared laser and a detector, such as a CMOS sensor, that captures three-dimensional imagery of the patient 110 and the surroundings (such as the medical devices surrounding and coupled to the patient). The images and/or video that are captured by the camera 104 can be processed locally or remotely, as described further below, to detect the actions of the patient 110.

For example, as depicted, the camera 104 is programmed to transmit the captured infrared imagery to the computing device 106 and/or directly to a server computer 122 through a network 120. The server computer 122 can be a central server that is programmed to process the imagery and/or allow the caregivers 212 to monitor the patient 110. Further, various alerting can be provided to the caregivers 212, as describe below. In another example, the server computer 122 can be an electronic medical record (EMR) repository, and the imagery and/or data associated therewith can be captured within the EMR for the patient 110.

In yet other embodiments, the computing device 106 and/or the server computer 122 are programmed to analyze the imagery of the patient 110 and the environment 102 to determine patient progress, compliance, and/or safety/risk.

The imagery can, for example, be analyzed to determine whether or not the patient is performing the proper actions using the proper form. As described further below, the system 100 can be programmed to make recommendations and/or modifications to the physical therapy when the system determines that the patient is proceeding at a slower or faster rate of recovery.

Further, the imagery can be used to determine compliance, such as determining if the patient performed the actions as required. For example, the patient may be required to perform a certain number of repetitions for each exercise during a session, and the system 100 can be programmed to determine whether or not the proper actions were performed.

In yet other examples, the system 100 is programmed to determine risk associated with the physical therapy. This risk can take various forms. For example, the system can be programmed to determine how the patient's actions might impact the patient's health status and/or surroundings, such as medical devices in the vicinity of and/or coupled to the patient. The system 100 can provide feedback to the patient 110 and/or the caregivers 212, as described further below, if a safety concern is identified, such as actions performed by the patient that might displace or otherwise impact medical devices or other therapy being provided to the patient 110.

Further, the system 100 can be programmed to encourage the patient 110 to perform the physical therapy as provided on the display 210. Examples of such encouragement include gamification of the physical therapy sessions. In some embodiments, that includes providing rewards or other incentives for completion of a therapy session. In other embodiments, a social media platform is created so that patients can connect and compete against other patients as another form of encouragement. More details are provided below.

Figure 3:
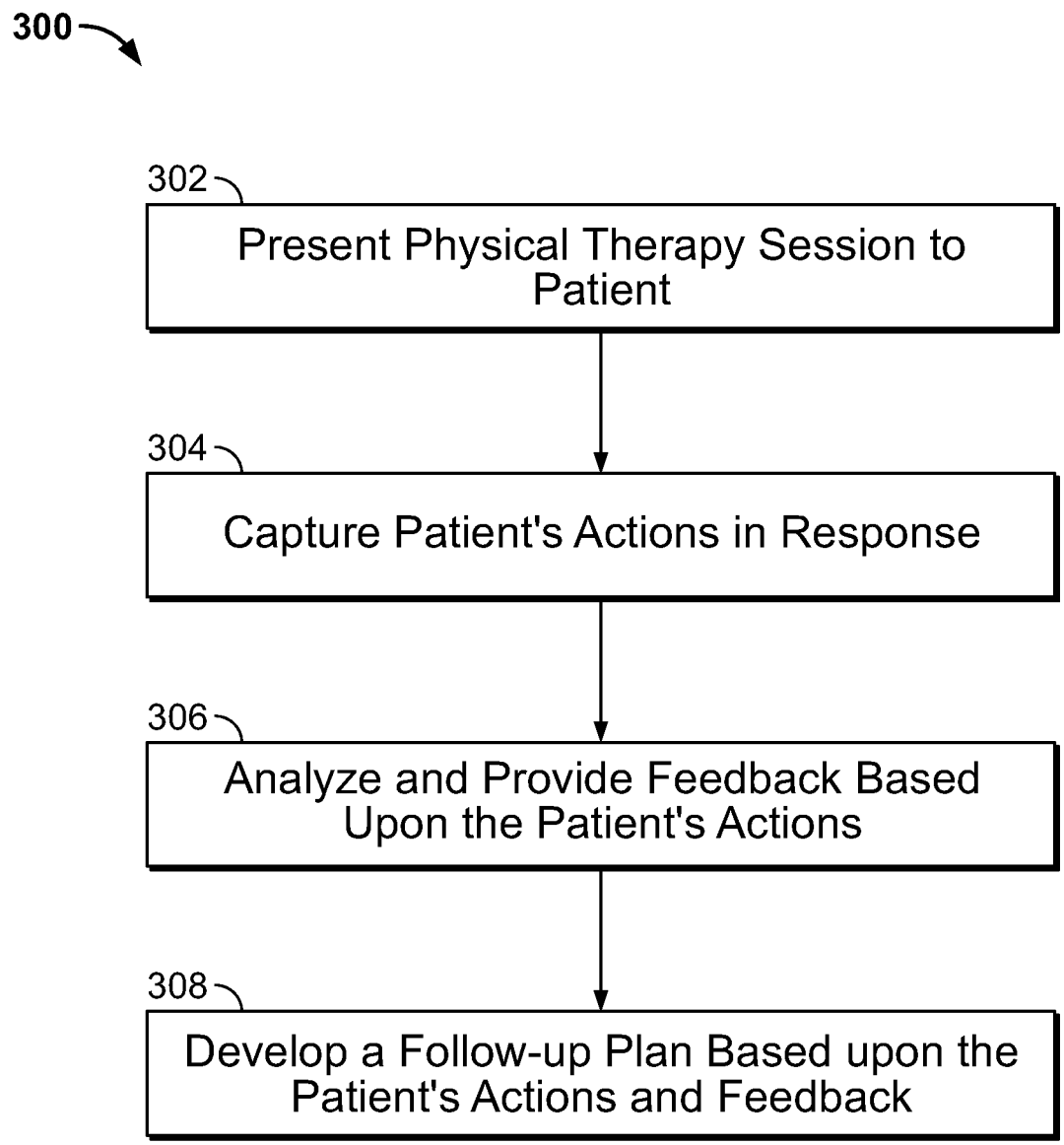
FIG. 3 shows an example method for assisting the patient to conduct physical therapy using the system of FIG. 1.

Referring now to FIG. 3, an example method 300 for providing a physical therapy session to a patient is shown. The physical therapy session can be created as a custom session selected by the patient's caregiver or can be automatically selected by the computing device based upon various criteria associated with the patient, such as age, gender, weight, health status, injury status, disease state, etc.

At operation 302 of the method 300, the physical therapy information is presented to the patient. As noted, this can be accomplished by displaying information about the physical therapy session to the patient on a display. This information can include text describing actions the patient should do, as well as images and/or videos of the actions themselves.

Next, at operation 304, the patient's actions are captured as images and/or video as the patient performs the physical therapy session. As described above, this can be done using one or more cameras that are used to capture the movement of the patient as the patient performs the actions during the physical therapy session.

At operation 306, the images and/or video are analyzed. As described above, this can include an automated analysis that determines such aspects as patient progress, compliance, and/or risk. Additional details on the aspects of this assessment are provided in FIG. 4 and described below.

Finally, at operation 308, a follow-up plan is developed based upon the analysis of the patient's action and feedback. This plan can include further physical therapy sessions and/or additional feedback to the patient. The plan can be developed automatically by the computing device as the patient's actions are analyzed. Or, suggested feedback can be developed and presented to a caregiver for review.

For example, a set of physical therapy sessions can be identified for the patient. Based upon the analysis of a physical therapy session, this set of physical therapy sessions (i.e., future sessions in the set) can be modified to accommodate the patient's actions and response to the physical therapy sessions.

Figure 4:
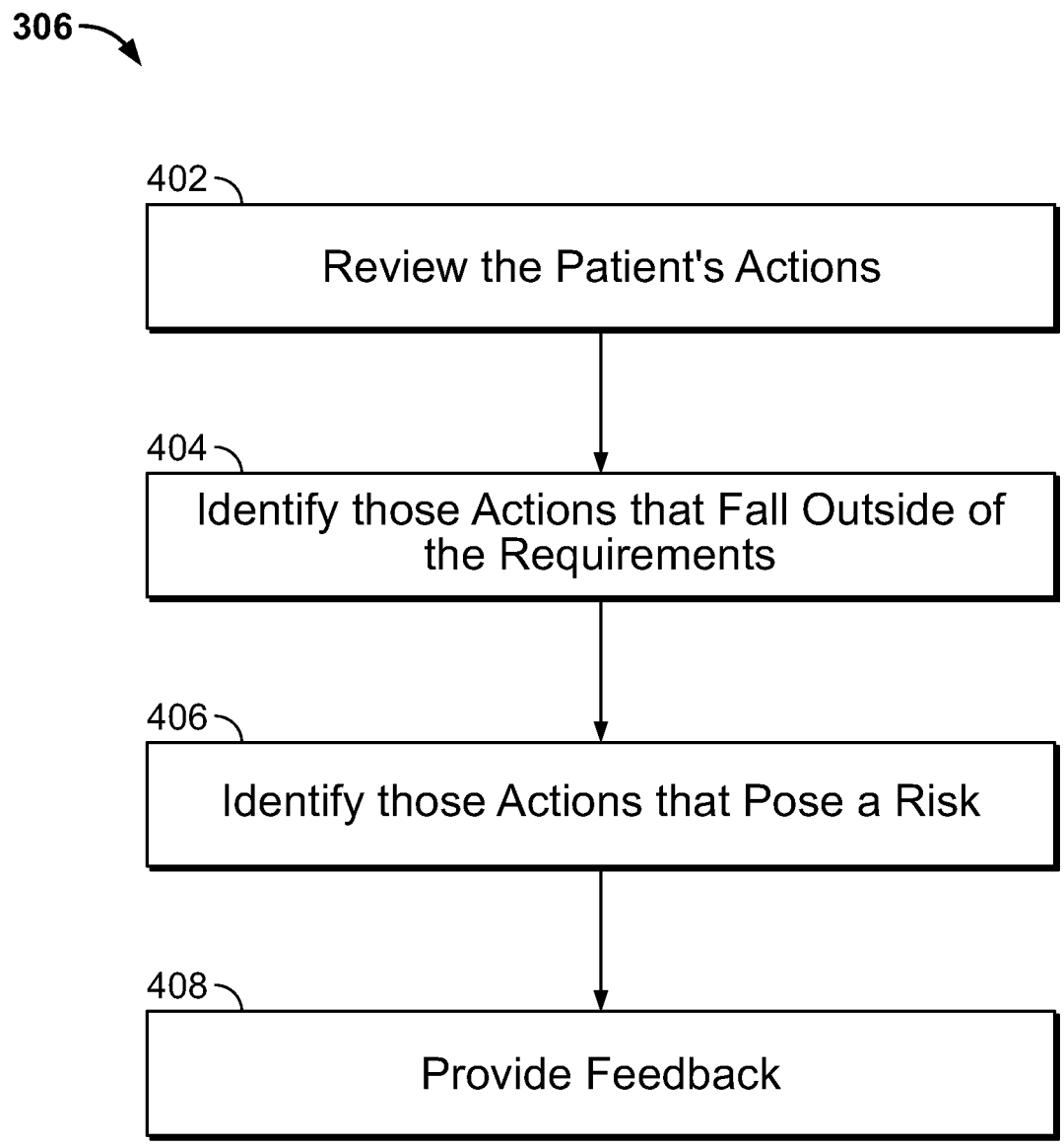
FIG. 4 shows additional details on the feedback step of the method of FIG. 3.

Referring now to FIG. 4, additional details regarding the analysis operation of operation 306 of the method 300 are shown.

At operation 402, the images and/or video of the patient performing the actions during the physical therapy session are analyzed. This can, for example, be accomplished by using pattern matching that compares the patient's movements to expected movements for the therapy. For example, if the patient is instructed to move her arm from a level horizontal position to an upright vertical position, the images and/or video can be analyzed to confirm that the patient performed the correct action(s) and the proper number of repetitions.

At operation 404, any actions by the patient that fall outside of the requirements for the physical therapy session are identified. Continuing with the example above, if the patient fails to move her arm to a full vertical position with each repetition, this failure can be identified. Or, if the patient only performs 5 repetitions when 10 repetitions were requested, this failure is identified.

Next, at operation 406, risks associated with the patient's actions during the physical therapy session are identified. These risks can include such issues as the patient's actions, such as over-extending or otherwise putting the patient at risk. The risk can also relate to the patient's medical therapies. For example, if the patient has a central line and is performing actions during physical therapy that might result in the dislodgement of the central line, the system can identify that risk.

Finally, at operation 408, the feedback is provided to the patient and/or caregiver. The feedback can be anything from additional directions for the patient to perform actions in a different manner, selection of different physical therapy sessions, and/or warnings to the patient regarding risky actions that might impact medical therapies that are being provided to the patient (e.g., "Do not swing your arms across your ventilator tubes because the motion could result in dislodgement.").

Figure 5:
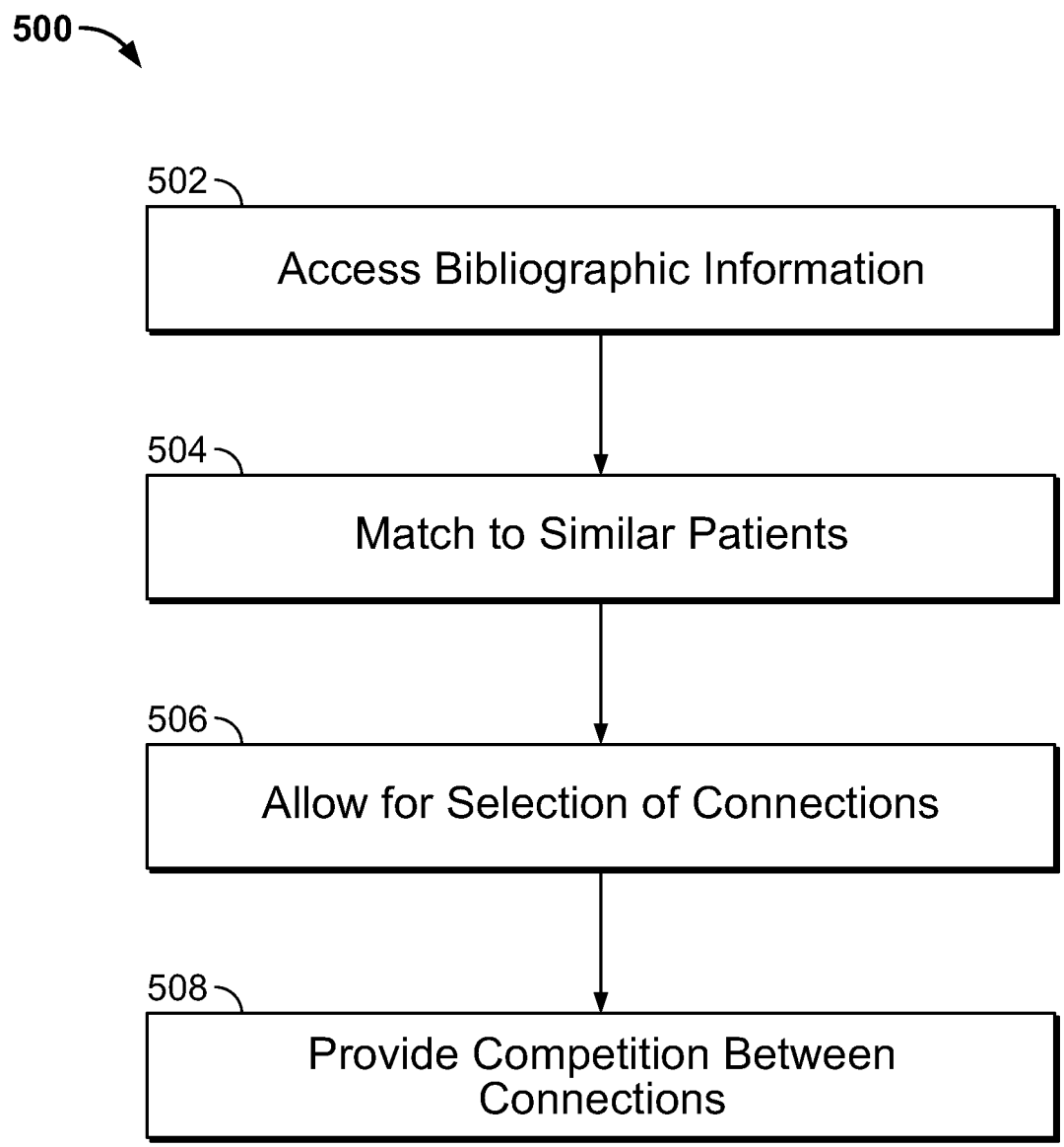
FIG. 5 shows an example method for gamifying physical therapy to encourage patients.

Referring now to FIG. 5, an example method 500 is shown for gamifying the physical therapy process to encourage compliance by the patient. In this example, a social media platform is created to allow the patient to connect with other patients.

At operation 502, information associated with the patient is accessed. This can be bibliographic information such as name, address, age, gender, injury state, disease state, etc. The privacy of the patient can be preserved by anonymizing the information and/or allowing the patient to control what, if any, information is shared.

Next, at operation 502, the bibliographic information is used to match the patient with other similar patients. This can be accomplished in many ways similar to that done on other social media platforms. For example, if the patient suffers from congestive heart failure as a disease state, the system may match the patient with other congestive heart failure patients of a similar age or in a similar geography.

At operation 506, the patient can select among different individuals and make connections. The connection between the patient and another patient allows the patient to communicate with that other patient, share information, and conduct physical therapy sessions in conjunction with that other patient. This process can include, for example, creating a messaging platform that allows the patients to encourage one another, post feedback and feelings associated with the physical therapy process, etc. In some examples, the patient can search for other patients based on various criteria and select desired patients for connections.

At operation 508, in one embodiment, the patient can enter into friendly competitions with the patient's connections. This could include such competitions as which connection is most consistent with completion of physical therapy sessions. Another example might be encouraging a patient to perform a certain number of repetitions or steps in competition with the patient's connections. Such competitions can be monitored to mitigate against unsafe conditions, such as physical over-extending a patient in a given health state.

The method 500 can help the patient to feel more connected and encouraged to complete each physical therapy session. The method 500 can build a sense of community that can span geography and assist each patient in recovery.

In alternative embodiments, other types of gamification can be applied. For example, in another embodiment, the patient can be awarded upon the successful completion of a physical therapy session. The award can take various forms, whether virtual or physical. For example, the patient can earn points for each success in the physical therapy process, and the points can be used at a later time to access premium content or purchase rewards. Other configurations are possible.

The systems and methods described herein can help to improve the balance and mobility of the patients in ICU settings or specific patient groups, such as patients who suffer from stroke. This physical therapy can help patients to regain muscle as well as energy, which helps the patients to leave the ICU earlier. The gamification of the physical therapy helps to improve the mental conditions and increases compliance which, in turn, helps the patients to recover more quickly.

Figure 6:
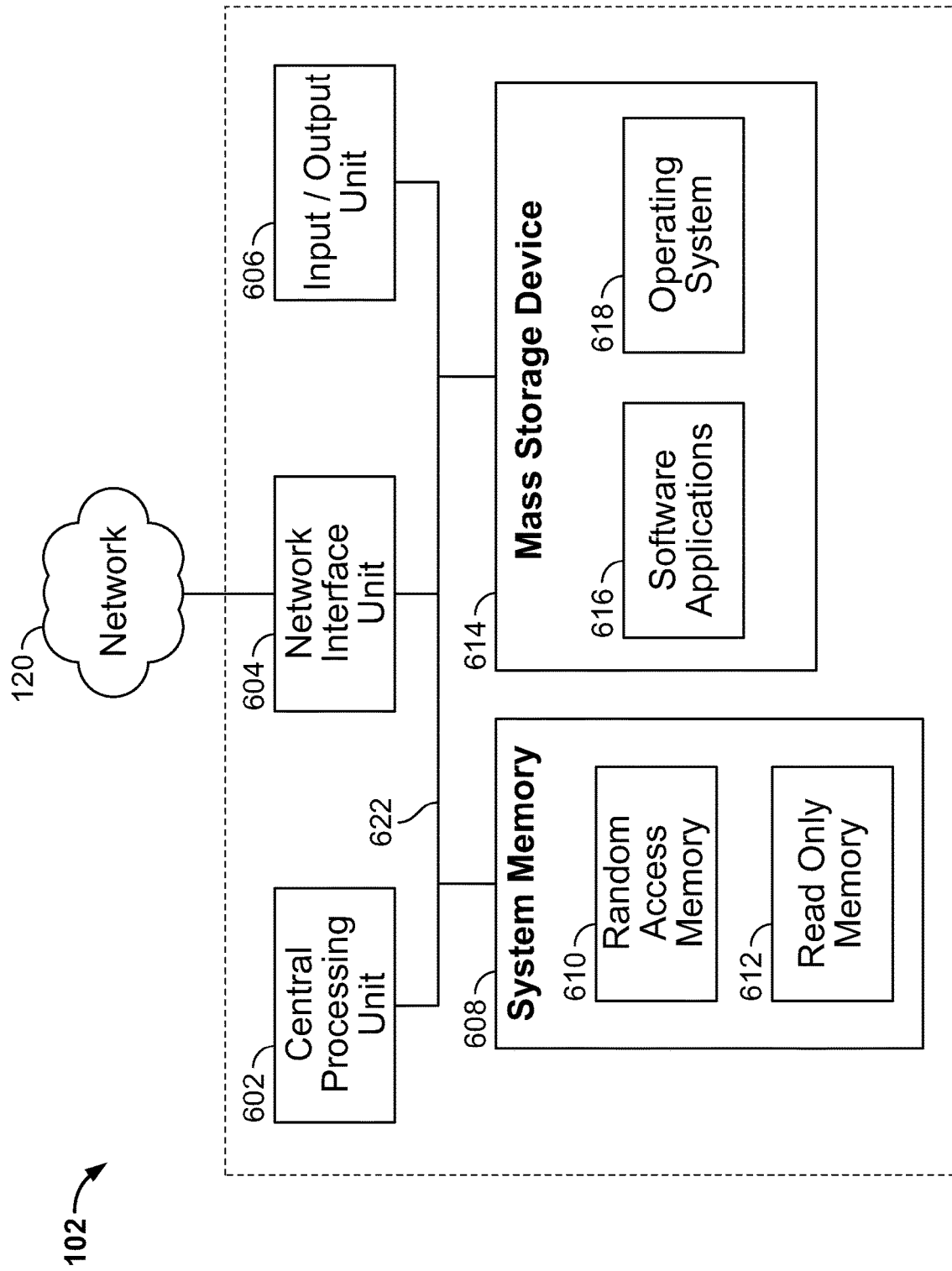
FIG. 6 shows example physical components of a computing device of the system of FIG. 1.

Referring now to FIG. 6, the computing device 106 (the server computer 122 can be similarly configured) includes at least one central processing unit ("CPU") 602, a system memory 608, and a system bus 622 that couples the system memory 608 to the CPU 602. The system memory 608 includes a random access memory ("RAM") 610 and a read-only memory ("ROM") 612. A basic input/output system contains the basic routines that help to transfer information between elements within the computing device 106, such as during startup, is stored in the ROM 612. The computing device 106 further includes a mass storage device 614. The mass storage device 614 is able to store software instructions and data.

The mass storage device 614 is connected to the CPU 602 through a mass storage controller (not shown) connected to the system bus 622. The mass storage device 614 and its associated computer-readable data storage media provide non-volatile, non-transitory storage for the computing device 106. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 106.

According to various embodiments, the computing device 106 may operate in a networked environment using logical connections to remote network devices through the network 120, such as a wireless network, the Internet, or another type of network. The computing device 106 may connect to the network 120 through a network interface unit 604 connected to the system bus 622. It should be appreciated that the network interface unit 604 may also be utilized to connect to other types of networks and remote computing systems. The computing device 106 also includes an input/output controller 606 for receiving and processing input from a number of other devices, including a touch user interface display screen, or another type of input device. Similarly, the input/output controller 606 may provide output to a touch user interface display screen or other type of output device.

As mentioned briefly above, the mass storage device 614 and the RAM 610 of the computing device 106 can store software instructions and data. The software instructions include software applications 616 and an operating system 618 suitable for controlling the operation of the computing device 106. The mass storage device 614 and/or the RAM 610 also store software instructions, that when executed by the CPU 602, cause the computing device 106 to provide the functionality of the computing device 106 discussed in this document.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for assisting a patient to conduct a physical therapy session, the method being implemented on a computing device comprising a system memory and at least one processing unit configured to execute instructions stored on the system memory, the method comprising:
   accessing, from the system memory with the at least one processing unit, bibliographic information for the patient, the bibliographic information including at least one of an injury state and a disease state;
   matching, using the at least one processing unit, the patient with one or more other patients based on similarities in bibliographic information;
   displaying information about the one or more other patients on an interactive display controlled by the at least one processing unit of the computing device;
   receiving, at the computing device, input from the patient selecting one of the other patients to communicate with;
   mediating communication between the patient and the selected other patient;
   receiving, at the computing device, input from the patient to enter into a joint therapy session with the selected other patient;
   initiating, with the at least one processing unit, a joint physical therapy session for treating the injury state and/or disease state of both the patient and the selected other patient;
   presenting information about the physical therapy session on the interactive display controlled by the at least one processing unit of the computing device, the information including one or more illustrative actions and movements required to be performed by the patient and the selected other patient;
   capturing, with one or more cameras in communication with the computing device, one or more images of the patient and one or more medical devices in the vicinity of the patient as the patient performs the movements during the physical therapy session;
   analyzing, by the at least one processing unit of the computing device, using the one or more images and pattern matching, the movements performed by the patient compared to the illustrative actions;
   detecting, by the at least one processing unit of the computing device, using the one or more images, the movements performed by the patient that pose a safety risk related to the one or more medical devices in the vicinity of the patient during the physical therapy session;
   generating feedback with the at least one processing unit regarding the safety risk and the performance of the patient; and
   displaying the feedback on the interactive display during the physical therapy session.

2. The method of claim 1, further comprising:
   detecting, by the at least one processing unit of the computing device, using the one or more images, a level of effort from the patient during the physical therapy session; and
   modifying, with the at least one processing unit, a future physical therapy session for the patient based upon the level of effort.

3. The method of claim 2, further comprising mediating a competition between the patient and the selected other patient during the physical therapy session based upon the level of effort.

4. A method for assisting a patient to conduct a physical therapy session, the method being implemented on a computing device comprising a system memory and at least one processing unit configured to execute instructions stored on the system memory, the method comprising:
   accessing, from the system memory with the at least one processing unit, the bibliographic information including at least one of an injury state and a disease state;
   matching, using the at least one processing unit, the patient with one or more other patients based on similarities in bibliographic information;
   displaying information about the one or more other patients on an interactive display controlled by the at least one processing unit of the computing device;
   receiving, at the computing device, input from the patient selecting one of the other patients to communicate with;
   mediating communication between the patient and the selected other patient;
   receiving, at the computing device, input from the patient to enter into a joint therapy session with the selected other patient;
   initiating, with the at least one processing unit, a joint physical therapy session for treating the injury state and/or disease state of both the patient and the selected other patient;
   presenting information about the physical therapy session on the interactive display controlled by the at least one processing unit of the computing device, the information including illustrative actions and movements required to be performed by the patient and the selected other patient;

capturing three-dimensional images of the patient with one or more infrared cameras as the patient performs movements in accordance with the illustrative actions during the physical therapy session;

automatically analyzing, by the at least one processing unit of the computing device using the three-dimensional images and pattern matching, the movements performed by the patient compared to the illustrative actions;

automatically assessing, by the computing device using the three-dimensional images, a level of effort from the patient during the physical therapy session;

displaying feedback generated by the at least one processing unit regarding the level of effort from the patient on the interactive display during the physical therapy session; and modifying, with the at least one processing unit, a future physical therapy session for the patient based upon the level of effort.

5. The method of claim 4, further comprising detecting, by the computing device, using the one or more images, a safety risk related to one or more medical devices in the vicinity of the patient during the physical therapy session.

6. The method of claim 4, further comprising analyzing the illustrative actions with the at least one processing unit to identify any movements in the one or more movements that fall outside of a required threshold.

7. The method of claim 4, further comprising mediating, using the at least one processing unit, a competition between the patient and the selected other patient during the physical therapy session based upon the level of effort.

8. A method for assisting a patient to conduct a physical therapy session, the method being implemented on a computing device comprising a system memory and at least one processing unit configured to execute instructions stored on the system memory, the method comprising:

accessing, from the system memory with the at least one processing unit, bibliographic information for the patient, the bibliographic information including at least one of an injury state and a disease state;

matching, using the at least one processing unit, the patient with one or more other patients based on similarities in bibliographic information;

displaying information about the one or more other patients on an interactive display controlled by the at least one processing unit of the computing device;

receiving, at the computing device, input from the patient selecting one of the other patients to communicate with;

mediating communication between the patient and the selected other patient;

receiving, at the computing device, input from the patient to enter into a joint therapy session with the selected other patient;

initiating, with the at least one processing unit, a joint physical therapy session for treating the injury state and/or disease state of both the patient and the selected other patient;

presenting information about the physical therapy session on the interactive display controlled by the at least one processing unit of the computing device, the information including one or more illustrative actions and movements required to be performed by the patient and the selected other patient;

capturing, with one or more cameras in communication with the at least one processing unit of the computing device, one or more images of the patient and one or more medical devices in the vicinity of the patient as the patient performs movements in accordance with the one or more illustrative actions and repetitions required during the physical therapy session;

analyzing the one or more images with the at least one processing unit of the computing device to compare movements of the patient with the one or more illustrative actions using pattern matching;

analyzing the one or more images with the at least one processing unit of the computing device to detect the movements of the patient that pose a safety risk related to the one or more medical devices in the vicinity of the patient;

detecting, by the at least one processing unit of the computing device, using the one or more images, a level of effort from the patient during the physical therapy session;

generating feedback with the at least one processing unit regarding the safety risk and the level of effort;

displaying the feedback on the interactive display during the physical therapy session; and allowing the patient to compete with other patients during the physical therapy session based upon the level of effort.

9. The method of claim 8, further comprising identifying any movements of the patient that fall outside of a required threshold for the physical therapy session using the at least one processing unit.

10. The method of claim 8, further comprising mediating, with the at least one processing unit, a competition between the patient and the selected other patient based upon the level of effort.

11. The method of claim 8, wherein the feedback comprises instructions to modify the patient's movements to reduce the safety risk.

12. The method of claim 8, further comprising automatically controlling a patient support device upon which the patient is resting, using the at least one processing device, to manipulate the patient's posture during the physical therapy session.

* * * * *